United States Patent [19]

Kazama et al.

[11] Patent Number: 4,480,474
[45] Date of Patent: Nov. 6, 1984

[54] METHOD AND APPARATUS FOR ULTRASONIC FLAW DETECTION OF T-WELDED PORTION OF STEEL PRODUCT

[75] Inventors: Hisao Kazama; Akito Nakanishi; Katsuichi Nakayama, all of Ibaragi, Japan

[73] Assignee: Sumitomo Metal Industries, Ltd., Osaka, Japan

[21] Appl. No.: 448,825

[22] Filed: Dec. 10, 1982

[51] Int. Cl.³ ............................................. G01N 29/04
[52] U.S. Cl. ......................................... 73/600; 73/614; 73/615
[58] Field of Search .................. 73/599, 600, 614, 615, 73/620, 642

[56] References Cited

U.S. PATENT DOCUMENTS 2,949,028  8/1960  Joy ........................................ 73/614
4,137,776  2/1979  Rudis et al. ........................... 73/615

Primary Examiner—Howard A. Birmiel
Attorney, Agent, or Firm—Burns, Doane, Swecker and Mathis

[57] ABSTRACT

Herein disclosed is a method for ultrasonic flaw detection of T-welded portion of steel product. The method comprises: maintaining the flange portion horizontally, making convergent ultrasonic beams incident on the flange portion vertically to the top face of the flange portion through a medium, scanning the incident beams transversely of the welded portion, detecting ultrasonic echo from a depth corresponding to the bottom face thickness of the flange portion, and comparing the level of said ultrasonic echo with a predetermined threshold value. Disclosed also is an apparatus for carry out the above method. These method and apparatus are suited particularly to the on-line flaw detection of the welded shape steel.

11 Claims, 20 Drawing Figures

DETECTION CHART OF FIRST PROBE

DETECTION CHART OF SECOND PROBE

METHOD AND APPARATUS FOR ULTRASONIC FLAW DETECTION OF T-WELDED PORTION OF STEEL PRODUCT

BACKGROUND OF THE INVENTION (1) Field of the Invention

The present invention relates to a method and apparatus for the ultrasonic flaw detection of a T-welded portion of a steel product.

More particularly, the present invention relates to a method and apparatus for the on-line ultrasonic flaw detection of a welded portion of a shaped steel product such as an H-beam.

(2) Description of the Prior Art

A steel product having a T-welded portion, for example, an H-beam is prepared by resistance welding of two steel strips corresponding to flanges and a steel strip corresponding to a web. For control of the quality of this welded H-beam, the welded portion should be inspected as specified in ASTM A-769.

As means for inspecting and guaranteeing the quality of welded H-beams, there have heretofore been adopted the following off-line methods; (1) a method in which the end face of an H-beam is directly inspected with the eye, (2) a method in which a test specimen having a length of 30 mm is sampled from a welded H-beam and this test specimen is subjected to an I-type tensile test, and (3) a method in which a test specimen having a length of 30 mm is sampled from a welded H-beam, the upper flange and web are bent down at a predetermined angle with the lower welded portion being as the center while the lower flange is fixed, to thereby impose a load on the lower welded portion, and the lower welded portion is inspected with the eye.

In these methods, however, since the off-line inspection system is adopted, it sometimes happens that when a defect is detected at the inspection stage, considerable amounts of defective products have already been produced in the production line, resulting in reduction of the yield. Moreover, this inspection is a laborious work and the quality is not completely guaranteed because the test is a sampling test.

Under such background, we conducted research with a view to developing a method for inspecting the entire surface of the welded portion in the production line by utilizing the ultrasonic flaw detection method.

However, it was found that it is very difficult to precisely inspect a T-welded portion of a shape steel according to the conventional ultrasonic flaw detection technique.

FIG. 1 schematically illustrates a method of the flaw detection of a T-welded portion according to the partial water penetrating test technique.

In the conventional method illustrated in FIG. 1, flanges 1F and 1F' of an H-beam 1 are horizontally arranged, and parallel ultrasonic beams 2 are applied downward to the upper face of the upper flange 1F. The flaw detection system comprises a frame member 3 forming, together with the top face of the flange 1F, a vessel containing a medium 4 such as water therein and a detecting probe 5 immersed in the medium. According to this method, the parallel ultrasonic beam 2 are incident on the welded portion from the detecting probe 5, and a flaw echo is checked.

In this method, however, since the ultrasonic beams 2 are simultaneously incident on the non-welded portion as well as on the welded portion, a wave form in which the flaw echo is overlapped on the bottom face echo is produced, and discrimination of the flaw echo is very difficult and a complicated electronic processing system becomes necessary for detection of the flaw echo. This disadvantage will now be described in detail with reference to FIG. 2. FIG. 2 is a schematic view showing the stage where parallel beams from the detecting probe 5 are incident on the welded portion 6 including a flaw, and the lower portion thereof shows a cathode-ray tube wave form of reflected waves, which is illustrated according to the single side deflection method. In case of T-shape welding, since the flaw is present substantially on the same level as the bottom face of the flange 1F, as shown in FIG. 2, there is produced a wave form in which a flaw echo F is overlapped on a bottom face echo B, and the increase of the echo level by the flaw echo F is small and discrimination of the flaw echo F is difficult. In FIG. 2, S represents a surface echo.

Moreover, if the surface of the flaw portion is rough and is inclined to the incident direction of the beams, the echo height of the flaw echo is low, and reduction of the detection precision is often caused.

SUMMARY OF THE INVENTION

It is a primary object of the present invention to solve the above-mentioned problems involved in the conventional technique and provide a method for the ultrasonic flaw detection of a T-welded portion of a steel product in which the detection can be performed with high precision.

Another object of the present invention is to provide a relatively simple method and apparatus in which the ultrasonic flaw detection of a T-welded portion of a steel product can be performed with a high precision in continuous manner in the production line.

Still another object of the present invention is to provide a method and apparatus for the ultrasonic flaw detection, in which the entire T-welded portion of a steel product can be inspected with high precision and the size of the defect can easily be measured.

In accordance with one fundamental aspect of the present invention, there is provided a method for the flaw detection of a T-welded portion of a steel product formed by T-welding a web member to a flange member, which comprises maintaining the flange portion horizontally, making convergent ultrasonic beams incident on the flange portion vertically to the top face of the flange portion from the top face of the flange portion through a medium, scanning the incident beams transversely of the welded portion, detecting ultrasonic echoes from a depth corresponding to the bottom face thickness of the flange portion, and comparing the level of said ultrasonic echoes with a predetermined threshold value.

By the term "convergent ultrasonic beams" used herein, there are meant ultrasonic beams oscillated from a vibrator through a sonic wave lens or the like. It is preferred that ultrasonic beams be convergent on the position of the bottom face of the flange where there is a possibility of the presence of a weld flaw.

In accordance with one embodiment of the above-mentioned method of the present invention, when the level of said ultrasonic echo is higher than the threshold value, said ultrasonic echo is judged as an echo from the bottom surface of the flange or from a flaw in the welded portion. Most of flaws of a T-welded portion formed by the resistance welding are weld flaws appearing in the vicinity of the position of the bottom face of the flange. According to the present invention, when the level of the echo is higher than the threshold value at an incident position corresponding to the welded position, it is judged that a flaw is present. Namely, in the method of the present invention, since the convergent area of ultrasonic waves is sufficiently small at the position corresponding to the bottom face of the flange, any echo should not be present in a healthy area of the welded portion.

In accordance with another embodiment of the abovementioned method of the present invention, incident position pulses synchronous with scanning of the incident ultrasonic beams are counted when the level of the ultrasonic echo is lower than the threshold value, and the count number is compared with a reference value to judge whether or not a flaw is present in the welded portion.

Namely, in the case where an echo corresponding to the bottom face thickness of the flange is not present, this indicates a healthy welded portion, and the difference between the length of the thus determined healthy welded portion and the weld width corresponds to the length of a weld flaw.

In accordance with one feature of the present invention, the steel product is a long article such as an H-beam and this steel product is transferred in the longitudinal direction threreof.

According to still another embodiment of the present invention, a plurality of ultrasonic wave detecting probes are aligned above the top face of the flange portion transversely of the welded portion and said probes are actuated in succession to scan the ultrasonic beams.

In accordance with another fundamental aspect of the present invention, there is provided an apparatus for the flaw detection of a T-welded portion of a steel product formed by T-welding a web member to a flange member, which comprises means for transferring the steel product while maintaining the flange portion horizontally, a frame member defining, together with the top face of the flange portion of the steel product being transferred, a vessel containing a medium therein, means for supplying the medium in said vessel, a convergent ultrasonic wave detecting probe disposed in said vessel to make ultrasonic waves incident on the top face of the flange substantially vertically to the top face of the flange through said medium, means for scanning ultrasonic beams of said detecting probe transversely of the welded portion, means for detecting echoes of the ultrasonic waves from a depth corresponding to the bottom face of the flange portion, and means for discriminating a flaw of the welded portion by synchronizing the detection of said echoes with the scanning position of said ultrasonic beams.

In accordance with one feature of the abovementioned apparatus of the present invention, the means for detecting echoes from a depth corresponding to the bottom face comprises a means for amplifying and detecting received waves of the probe, which is connected to said detecting probe, and means for comparing an output signal from said wave detecting member with a predetermined threshold value.

It is preferred that the threshold value be determined so that the threshold value corresponds to the echo height of the beams incident on the starting point of the healthy welded portion. If the output signal of the wave detecting member is lower than the threshold value, the echo is that from the healthy weld portion. If this output is higher than the threshold value, the echo is that of the bottom face of the flange portion or that of a flaw.

In accordance with another feature of the apparatus of the present invention, the flaw discriminating means comprises a circuit generating a gate signal when the output of the wave detecting member is lower than the threshold value, an oscillator for generating pulse signals corresponding to the position of the detecting probe, a counter to be actuated said gate signal to count said position pulse signals and a memory for storing the count value of said counter.

In accordance with still another feature of the apparatus of the present invention, the memory and the counter are constructed so that the memory receives a holding signal in correspondence to termination of one scanning of the detecting probe and the counter is reset after an elapse of a predetermined time from the time of termination of said one scanning.

According to one embodiment of the apparatus of the present invention, the ultrasonic flaw detecting means comprises a plurality of detecting probes arranged in the vessel of the medium to traverse the T-welding line and the means for scanning the ultrasonic beams comprises a changeover switch for actuating said detecting probes in succession.

Other objects, features and advantages of the present invention will become apparent from the following description made with reference to embodiments illustrated in the accompanying drawings.

DETAILED DESCRIPTION OF THE PREFERRED EMBODIMENTS

Figure 1:
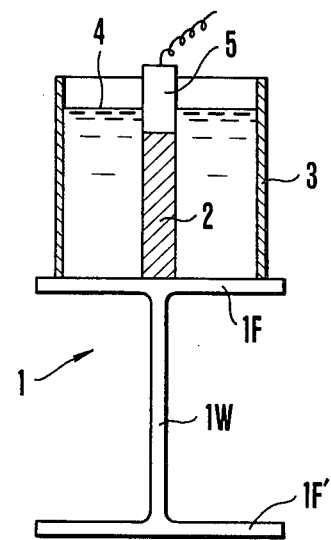
FIG. 1 is a diagram illustrating schematically the conventional method for the ultrasonic flaw detection of an H-beam.
Figure 2:
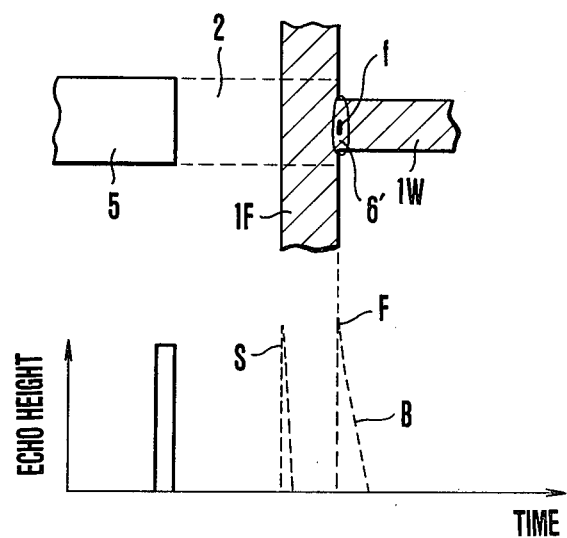
FIG. 2 is a diagram showing the state where a welded portion including a flaw f is detected according to the method shown in FIG. 1, together with a cathode-ray tube wave form of reflected waves in the method shown in FIG. 1.

The basic features of the present invention will first be described with reference to FIG. 3. Incidentally, in the accompanying drawings, the same or corresponding members are represented by the same reference numerals.

Figure 3:
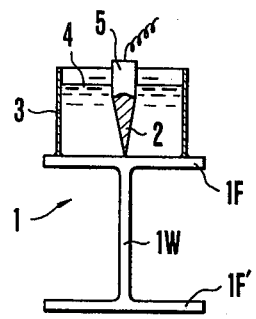
FIG. 3 is a diagram illustrating the flaw detection of a T-welded portion according to one embodiment of the method of the present invention.

Referring to FIG. 3, an ultrasonic wave detecting probe 5 is of the convergent type, and ultrasonic beams 2 are made incident on the top face of an upper flange 1F of a shaped steel product through a medium (water in this embodiment) by this detecting probe 5. It is preferred that the focus of the detecting probe 5 be located on the lower face of the flange 1F, which is the object of the flaw detection. If the focus of the detecting probe 5 is located at a lower position, a weld bead echo is picked up as a noise and if the focus is located at a higher position, the resolving power is reduced at the lower face of the flange 1F.

It is preferred that the distance in water between the oscillating portion of the detecting probe 5 and the top face of the flange 1F be 5 to 10 mm. If this distance is smaller than 5 mm, there is a risk of scratching or damage to the surface of the flange 1F because of contact of the detecting probe 5 with the surface of the flange 1F according to the surface condition of the shaped steel or by vertical vibrations during the transportation. If this distance is larger than 10 mm, there would be an attenuation of the incident beam and as a result a decrease in sensitivity. In order to enhance the resolving power, it is preferred that the beam diameter on the bottom face of the flange 1F be as small as possible. For example, the beam diameter may be adjusted to about 0.25 mm. In the present embodiment, a convergent detecting probe having an oscillator diameter of 6 mm, a detection frequency of 10 MHz and a focal distance of 15 mm is used, and a beam diameter of about 0.5 mm is obtained.

It is preferred that the width of scanning the incident beams be about 2 times the thickness of the web 1W. The reason is that the deposition width of the weld is 1.3 to 1.5 times the thickness of the web and the mechanical deviation of the measurement system is taken into consideration.

While the shape steel 1 is transferred in the longitudinal direction thereof (in the front-rear direction as presented in FIG. 3) and the detecting probe 5 is vibrated at 20 to 50 Hz in the left-right direction, that is, transversely of the weld line of the shape steel, an echo from the bottom face of the flange or an echo from a flaw is inspected.

Figure 4:
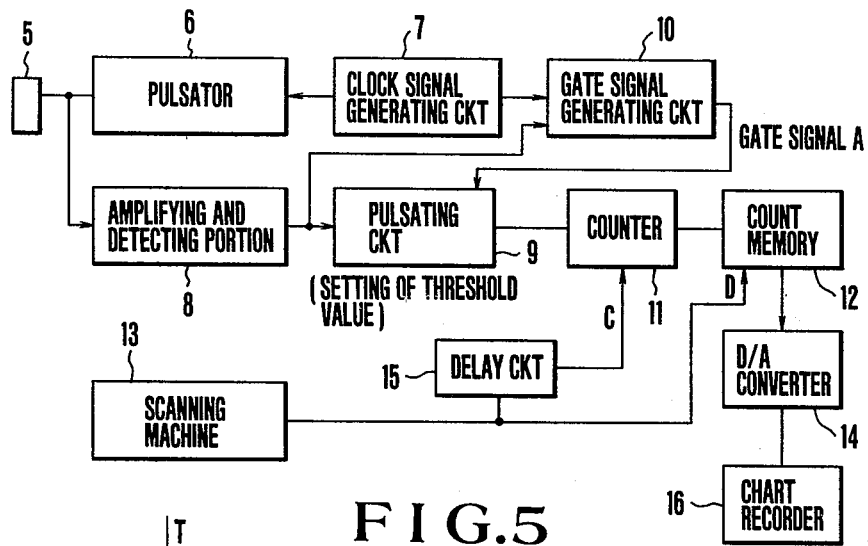
FIG. 4 is a flow chart showing the processing of signals used in the method shown in FIG. 3.

FIG. 4 is a block diagram illustrating the signal processing system according to the present invention. As shown in FIG. 4, the detecting probe 5 is excited and vibrated at a repetition frequency of, for example, 3000 pulses/second by a pulsator 6 synchronous with a clock means 7. On the other hand, reflected waves received by the detecting probe 5 are amplified and detected by an amplifying and detecting portion 8 and inputted to a pulsating circuit 9.

The pulsating circuit 9 is constructed so that when the output of the detecting portion within the time of a gate signal set by a gate signal generating circuit 10 is lower than a predetermined threshold value, an event pulse E is outputted in correspondence to the repetition frequency.

Figure 5:
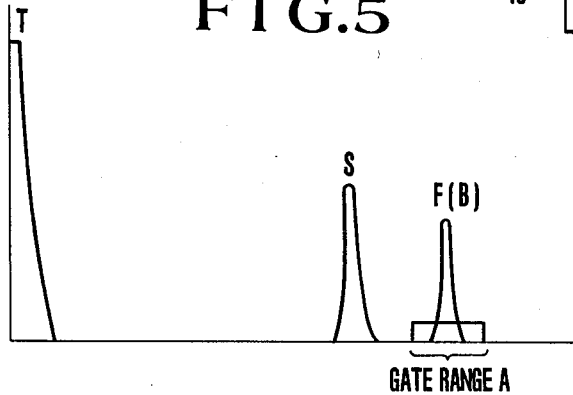
FIG. 5 is a cathode-ray tube wave form diagram of signals obtained according to the method of the present invention, which illustrates the relation to the gate signal A shown in FIG. 4.

The gate signal generating circuit 10 receives the output of the clock means 7 and the output of the detecting portion and it outputs a gate signal A corresponding to the time range of appearance of a bottom face echo B or a flaw echo F in each vibrating pulse of the detecting probe 5 as shown in FIG. 5. More specifically, the gate signal generating circuit receives an oscillating pulse T of the detecting probe from the detecting portion 8 and outputs a predetermined time range given by the clock means 7 as the gate signal A.

The threshold value to be compared with the output within the range of the gate signal A of the amplifying and detecting portion in the pulsating circuit 9 will now be described with reference to FIG. 6.

Figure 6:
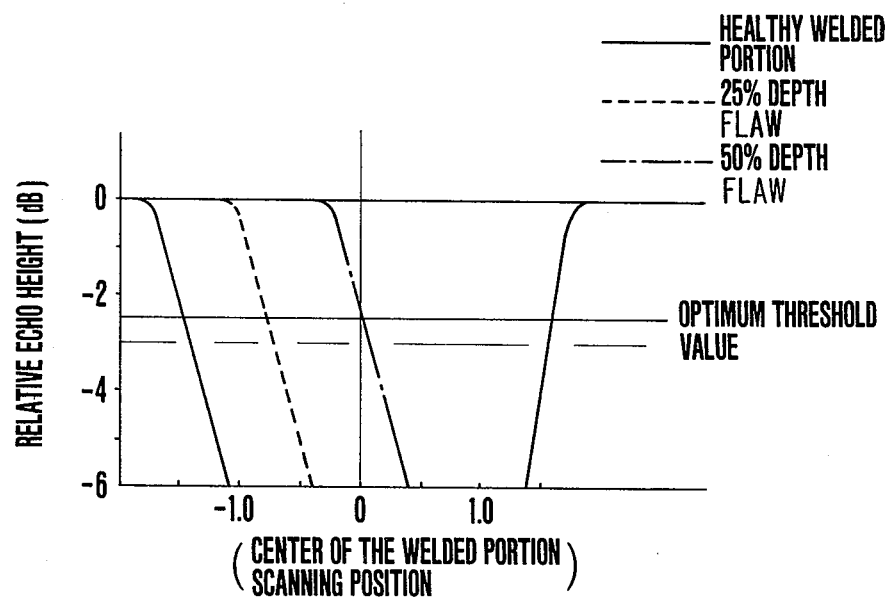
FIG. 6 is a diagram showing bottom face echoes and flaw echoes of various welded portions, together with flaw-including T-welded portions.
Figure 6:
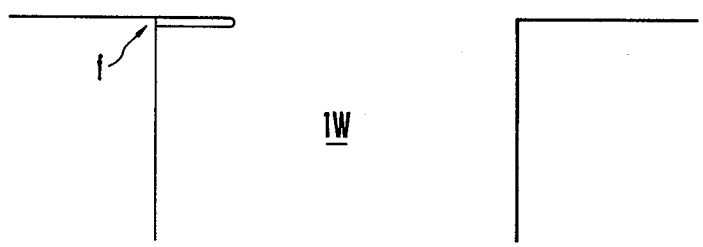

FIG. 6 shows echo heights within the gate signal A, obtained when various welded portions (a healthy welded portion, a welded portion having a 25% depth flaw and a welded portion having a 50% depth flaw) as shown in the lower portion of FIG. 6 are scanned by the convergent detecting probe 5, in comparison with the scanning positions. Two kinds of flaws f (one having a length of 12.5 mm and a depth corresponding to 25% of the web thickness and the other having a length of 25 mm and a depth corresponding to 50% of the web thickness) are formed on the flange 1 (having a thickness of 4.5 mm and a width of 100 mm) and the web 1W (having a height of 100 mm and a thickness of 3.0 mm) by the discharge treatment, as shown in the lower portion of FIG. 6.

As shown in FIG. 6, in case of the healthy welded portion, the echo height at the point apart from the center of the welded portion by ±1.15 mm, which corresponds to the distance between the center of the welded portion and the end of the web width, is about −2.5 dB. Accordingly, if this value of −2.5 dB is adopted as the threshold value, a reflected wave having a level lower than −2.5 dB may be judged as a bottom face echo or flaw echo.

Figure 7:
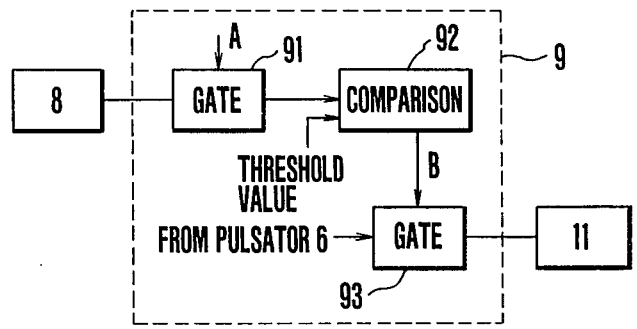
FIG. 7 is a diagram illustrating one embodiment of the pulse generating circuit shown in FIG. 4.

The pulsating circuit 9 shown in FIG. 1 outputs an event pulse E when the level of the output detected within the range of the gate signal A is lower than the threshold value. FIG. 7 is a block diagram showing one embodiment of the pulsating circuit 9.

As shown in FIG. 7, the pulsating circuit 9 comprises a first gate 91 which receives the output of the detecting portion 8 and is opened by the gate signal A, a comparator 92 which receives the output of the detecting portion having a gate width A on one input through the first gate 91 and the threshold value on the other input, compares them and outputs a gate signal B when the output of the detecting portion is lower than the threshold value, and a second gate 93 which receives pulses of the repetition frequency from the pulsator and is opened by the gate signal B from the comparator 92. The second gate 93 outputs event pulses E to a counter 11. Accordingly, of vibrating pulses of the detecting probe 5, the pulses are counted by the counter 11 only when reflected waves having a level lower than the threshold value within the gate range A are detected.

Referring to FIG. 4 again, the event pulses E counted by the counter 11 are supplied to a memory 12, and the count value in the memory 12 is held by a signal D indicating changeover of the scanning direction, which is fed from ultrasonic beam scanning means 13, and is outputted into a D/A converter 14. On the other hand, a reset signal C delayed by a predetermined time, for example, 10 microseconds, is inputted to the counter 11 from the scanning means 13 through a delay circuit 15 to reset the count value and prepared for the counting at the subsequent scanning in a different direction.

The D/A converter 14 outputs an analog value corresponding to the length of the healthy welded portion into a chart recorder 16 to record the analog value therein. There may be adopted a method in which a signal of the position of the shape steel 1 with respect to the longitudinal direction is inputted to the chart recorder 16 and results of the flaw detection at the positions in the longitudinal direction are recorded.

The mechanism for scanning ultrasonic beams according to one embodiment of the present invention will now be described with reference to FIG. 8. FIGS. 8(a) and 8(b) are side and plan views illustrating diagrammatically this scanning mechanism.

As shown in FIG. 8, the detecting probe 5 is arranged in a case 17, and the case 17 is connected to an arm 18 supported in a sleeve 19 so that it can slide in a reciprocating manner. The arm 18 is connected to a rod 20 through a pin 21 and the other end of the rod 20 is connected to a rotary disc 22 through a pin 23. The rotary disc 22 is rotated and driven by a motor 25 through a gear mechanism 24. Since the pin 23 is eccentric to the rotary disc 22, the arm 18 and the rod 20 constitute a piston-crank mechanism, and the rotation of the motor 25 is converted into reciprocating movement of the arm 18. Therefore, the detecting probe 5 makes a reciprocating movement at a right angle to the weld line of the shape steel 1 while retaining a vertical posture to the top face of the flange 1F.

Incidentally, the reset signal C from the scanning means shown in FIG. 4 and the latch signal D may be produced by a pulse oscillator (not shown) attached to the motor 25.

Figure 8A:
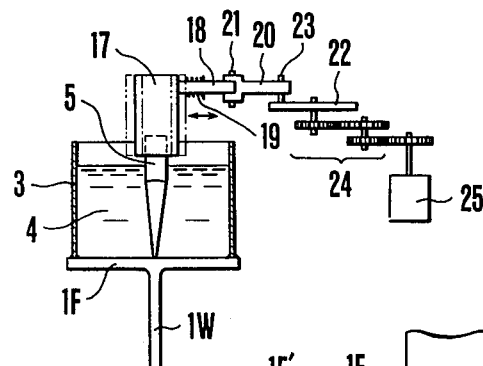
FIG. 8(a) is a side view illustrating diagrammatically a mechanical mechanism for giving a reciprocating movement to the detecting probe.
Figure 8B:
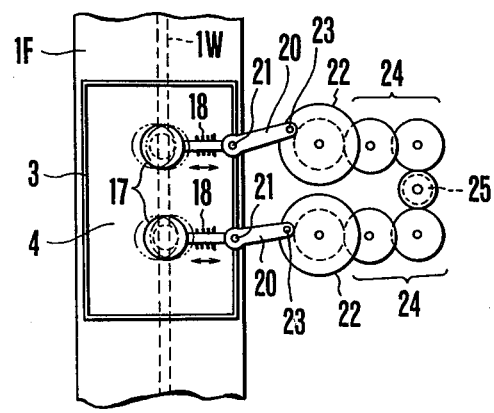
FIG. 8(b) is a plan view illustrating diagrammatically said mechanical mechanism.
Figure 9A:
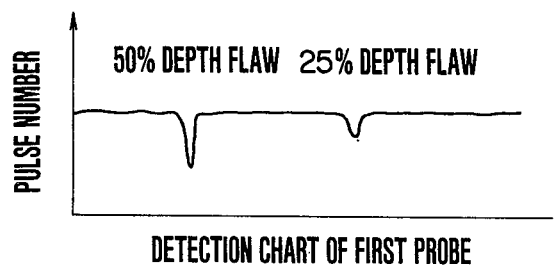
FIGS. 9(a) and 9(b) show examples of results of the flaw detection of the welded portion by the apparatus of the present invention.
Figure 9B:
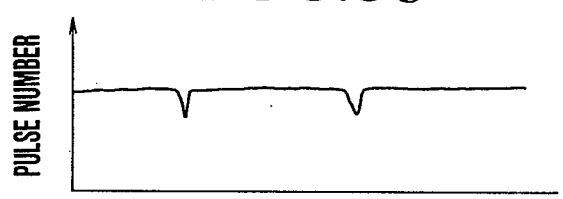

Records shown by the chart recorder 16 when welded portions containing artificial 25% and 50% flaws are detected by the two detecting probes shown in FIGS. 8(a) and 8(b) and the signal processing is carried out by the signal processing system shown in FIG. 4 are illustrated in FIGS. 9(a) and 9(b). FIG. 9(a) shows a record chart showing the results of the flaw detection by the first detecting probe 5 and FIG. 9(b) shows a record chart the results of the flaw detection by the second probe 5'. In the drawings, the abscissa indicates the time, that is, the position in the longitudinal direction of the shape steel, and the ordinate indicates the length corresponding to the number of pulses counted by the counter 11 (that is, the flaw-free weld width).

A second embodiment of the present invention will now be described with reference to FIGS. 10 through 13.

Figure 10:
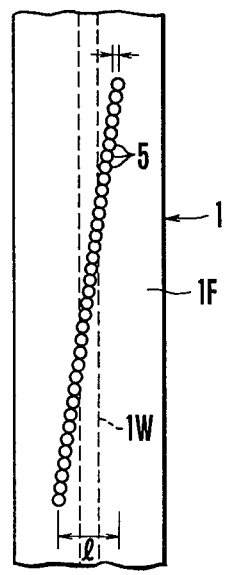
FIGS. 10 and 11 are plan and side views showing the arrangement of detecting probes according to a second embodiment of the flaw detection method of the present invention.
Figure 11:
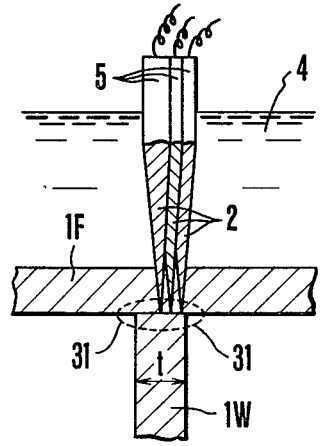

FIG. 10 is a plan view showing the positional relation between detecting probes and the upper flange 1F in the present embodiment, and FIG. 11 is a front view showing this relation. As shown in FIGS. 10 and 11, the detecting probes 5 are arranged at intervals P in the width direction of the flange 1F along a length in the width direction, which covers at least a welded portion 31. Each detecting probe 5 emits ultrasonic beams 2 vertically to the top face of the flange 1F through a medium 4. It is preferred that these ultrasonic beams be convergent at the position of the bottom face of the flange 1F.

Figure 12:
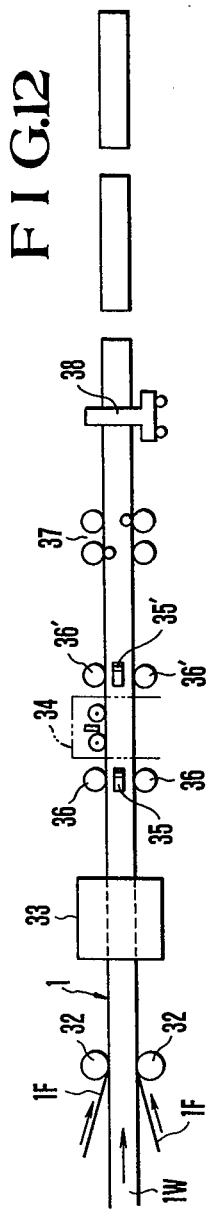
FIG. 12 is a diagram illustrating schematically the production and inspection line of H-beams, which includes the ultrasonic flaw detection apparatus of the present invention.

FIG. 12 is a diagram illustrating schematically the production and inspection line of welded H-beams to which the apparatus of the present embodiment is preferably applied.

As shown in FIG. 12, a welding machine forms an H-beam by resistance welding of three steel strips being transported, that is, flanges 1F and 1F' and a web 1W. The welded H-beam is cooled in a water cooling zone 33 and subjected to ultrasonic flaw detection of the welded portion 31 by the ultrasonic flaw detecting apparatus 34 according to the present invention. The line speed of the H-beam in the flaw detection apparatus 34 is, for example 70 m/min. In order to stabilize the running posture of the H-beam 1 in both the vertical and horizontal directions in the flaw detecting apparatus 34, it is preferred that horizontal guide rollers 35 and 35' and upper and lower press rollers 36 and 36' be disposed on the front and rear sides of the flaw detecting apparatus 34. After the flaw detection, the H-beam 1 is pased through a straightening machine 37, cut into a predetermined length by a cutter 38 and transported to the subsequent finishing step.

Incidentally, in the drawings, only the flaw detecting apparatus 34 for the welded portion of the upper flange 1F is illustrated, but practically, a flaw detecting apparatus for the welded portion of the lower flange 1F' is appropriately arranged in the line.

Figure 13:
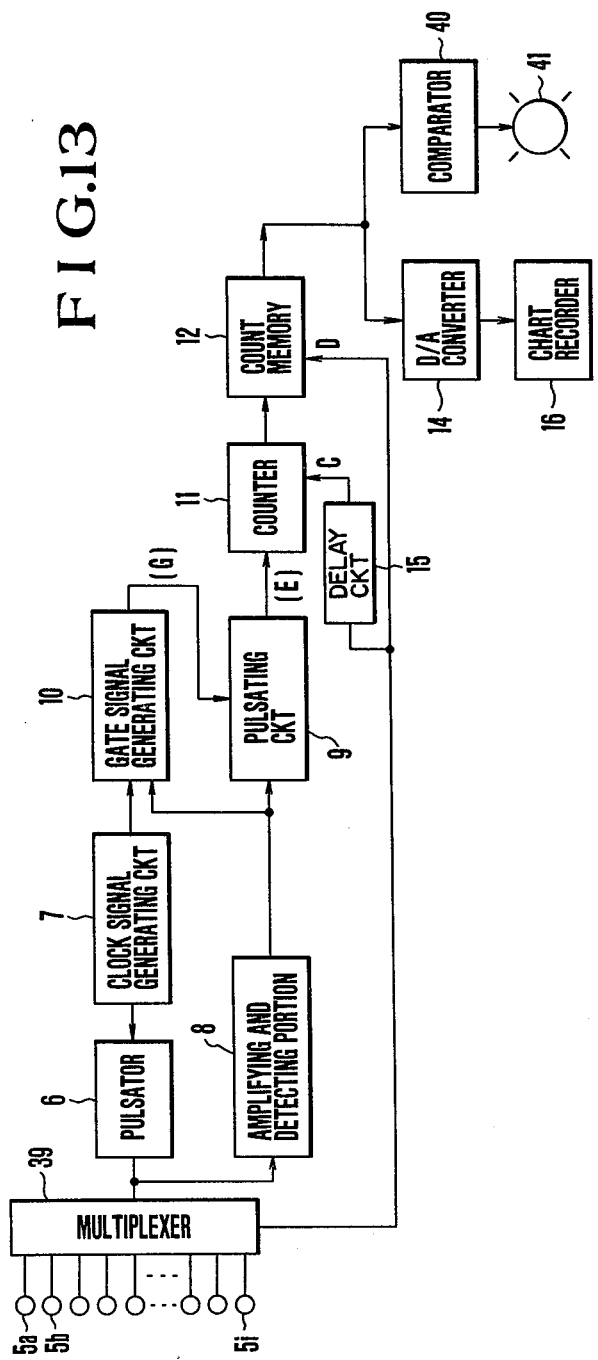
FIG. 13 is a block diagram illustrating a signal processing system used in the second embodiment of the present invention.

FIG. 13 is a block diagram showing a signal processing portion to be used when the flaw detection of the welded portion is carried out by using the detecting probes 5 shown in FIGS. 10 and 11. In FIG. 13, the same members as those of the signal processing portion shown in FIG. 4 are represented by the same reference numerals as shown in FIG. 4.

As shown in FIG. 13, detecting probes 5a through 5i are connected to an ultrasonic wave receiving and transmiting system through a multiplexer 39. The respective probes 5 are excited in succession according to the changeover operation of the multiplexer 39. The multiplexer 39 may be actuated synchronously with the transmission frequency of the pulsator 6 or another control signal may be inputted into the multiplexer.

For example, when the line speed in FIG. 12 is 70 m/min, the transmission frequency of the pulsator 6 is 3 KHz and about 10 probes are changed over in succession at 3 KHz by the multiplexer, the flaw detection of the welded portion of the H-beam can be effected at intervals of about 3.9 mm in the longitudinal direction.

Furthermore, when the time of one scanning of the multiplexer 39 is adjusted to 0.02 second, that is, when the respective probes are changed over at intervals of 0.002 second, each probe 5 transmits six pulses. In this case, the flaw detection is performed at intervals of about 2.3 mm in the longitudinal direction of the H-beam at the positions of the respective probes 5 with respect to the flange width direction, and the deviation between the first and final flaw detection positions within one scanning is about 140 mm. Namely, the flaw detection is performed at an inclination to the width direction of the flange 1F.

The selection of the changeover operation of the multiplexer 39 is made while the kind of the flaw to be detected and the line speed are taken into consideration. Incidentally, in the present embodiment, it is preferred that scanning of the probes be one-direction scanning, not reciprocating scanning.

In the drawings, reference numeral 40 represents a comparator for determining the presence or absence of a flaw from the count value of event pulses, and reference numeral 41 represents a lamp indicating the detection of the flaw.

The structure of the flaw detecting apparatus will now be described in detail with reference to FIGS. 14 through 18.

Figure 14:
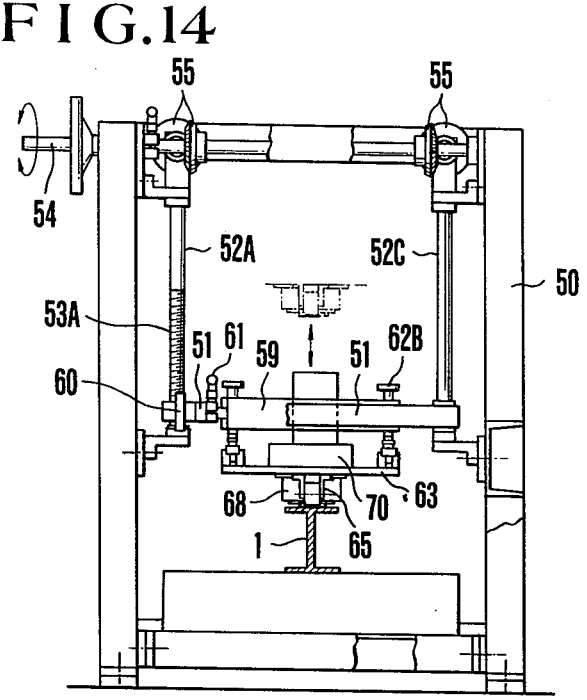
FIGS. 14, 15 and 16 are front, plan and side views showing a loading mechanism for arranging the flaw detection apparatus of the present invention on the production line.
Figure 15:
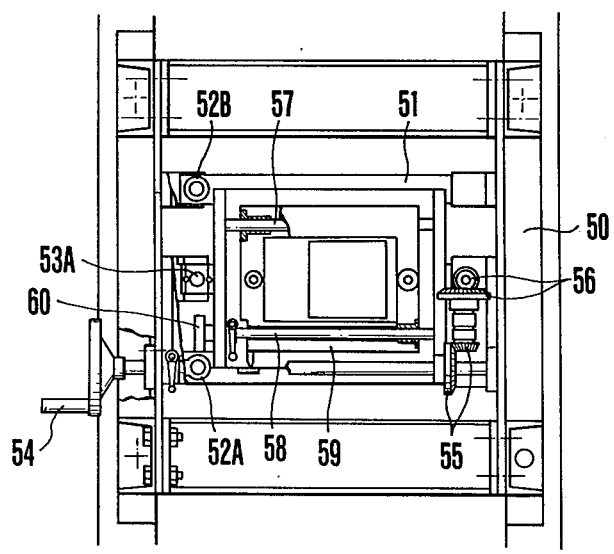
Figure 16:
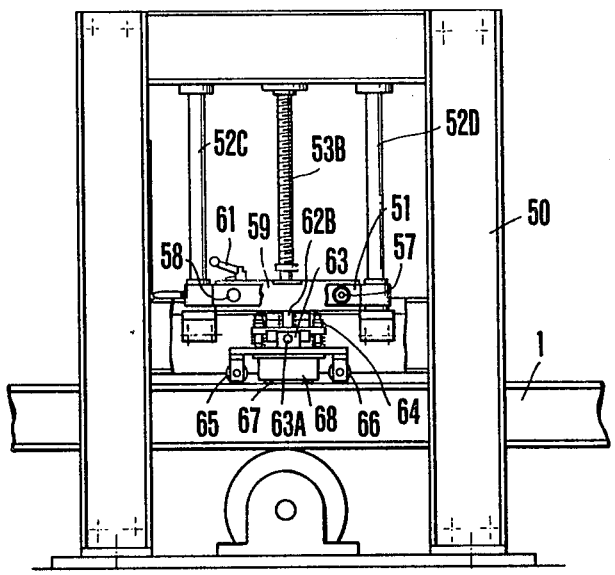

FIGS. 14, 15 and 16 are front, plan and side views of the loading structure for arranging the flaw detecting apparatus in the production line. Reference numeral 50 represents a stand comprising a framed shape steel and arranged astride of the transportation line, and reference numeral 51 represents a vertically moving frame which is guided by guide rods 52A through 52D attached to the stand 50 on the left and right sides of the line and secured to vertically moving screw rods 53A and 53B supported on the stand 50 at the center of the left-right line direction. The screw rods 53A and 53B are rotated by rotation of a vertically moving handle 54 through two bevel gears 55 and 56 to vertically move the vertically moving frame 51.

In the opening of the vertically moving frame 51, a horizontally moving frame 59 is supported on guide rod 57 and horizontally moving screw rod 58 which are arranged astride of the vertically moving frame 51 on the left and right sides thereof, and the frame 59 may be horizontally moved to the left and right by rotation of a horizontally moving handle 60. Reference numeral 61 represents a horizontally moving securing lever.

Below the horizontally moving frame 59, a probe attaching plate 63 is hung at the center of the left-right line direction through a pin 63a by hanging rods 62a and 62B. The probe attaching plate 63 is urged downward by a compression spring 64 mounted on the periphery of the hanging rods 62A and 62B. Profile rollers 65 and 66 are attached to the front and rear parts of the lower face of the probe attaching plate, and these rollers 65 and 66 abut against the top face of the flange 1F during the flaw detection.

Figure 17:
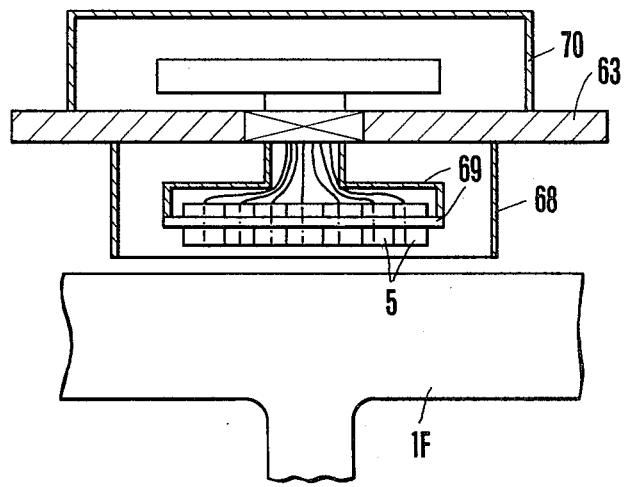
FIGS. 17 and 18 are side and bottom views showing an apparatus for attaching the probes.
Figure 18:
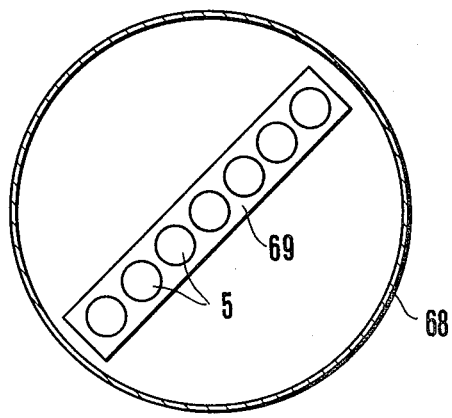

As shown in side and bottom views of FIGS. 17 and 18, a water tank 68 having a sealant 67 is disposed below the probe attaching plate 63, and a supporting casing 69 for supporting probes 5 is arranged in the water tank 68. Reference numeral 70 represents a probe changeover terminal.

In the flaw detecting apparatus having the abovementioned structure, the vertically moving handle 54 is operated at the time of the flaw detection to bring down the vertically moving frame 51 from the standing position indicated by an imaginary line in FIG. 14 to cause the profile rollers 65 and 66 to abut against the flange 1F. If the left-right position is deviated from the center of the H-beam, the horizontally moving handle 60 is operated to adjust the position of the horizontally moving frame 59.

During the flaw detection, even if the H-beam is moved in the vertical direction, since the compression spring 64 is disposed, the distance between the detecting probes and the H-beam is kept constant, and the probe attaching plate 63 is inclined back and forth to comply with the movement of the H-beam 1. At the flaw detection, the water tank 68 is filled with water as a contact medium.

Incidentally, also the flaw detecting apparatus for the lower welded portion has, in principle, the same structure as described above, but it is necessary to dispose means for supplying the medium so that the medium is always present between the probes and the lower flange and then the position for discharging the medium is located above the lower face of the lower flange.

As will be apparent from the foregoing description, according to the method of the present invention, it is possible to detect accurately with high detecting precision in a continuous manner in the production line whether or not a weld flaw is present, and therefore, the quality can be guaranteed very effectively and the production rate can be increased remarkably.

Furthermore, with the apparatus described hereinabove, the flaw detecting method can be carried out effectively, and since vertically moving means and profile rollers are disposed, the flaw detection of a variety of shape steels differing in the size can be performed stably while keeping the distance between the shape steel and probes constant.

The present invention has been described with reference to the embodiments illustrated in the accompanying drawings, but it must be noted that these embodiments are given only for illustration and the scope of the present invention is by no means limited by these embodiments.

Many modifications can be made within the technical scope defined by the appended claims, and it must be noted that these modifications are included within the scope of the present invention.

What is claimed is:

1. A method for the flaw detection of a T-welded portion of a steel product formed by T-welding a web member to a flange member, which comprises maintaining the flange portion horizontally, making convergent ultrasonic beams incident on the flange portion perpendicular to the top face of the flange portion through an ultrasonic transmission medium, scanning the incident beams transversely of the line of intersection between the flange member and the web member, detecting ultrasonic reflections from a depth corresponding to the thickness of the flange portion, and comparing the level of said ultrasonic reflections with a predetermined threshold value.

2. A flaw detection method according to claim 1, wherein when the level of an ultrasonic reflection is higher than the threshold value, said ultrasonic reflection is indicated to be a reflection from the bottom surface of the flange or from a flaw in the welded portion.

3. A flaw detection method according to claim 2, wherein when the level of a reflection is higher than the threshold value at an incident position corresponding to the welded position, it is indicated that a flaw is present.

4. A flaw detection method according to claim 1, wherein incident position pulses synchronous with scanning of the incident ultrasonic beams are counted when the level of the ultrasonic reflections are lower than the threshold value, and the count number is compared with a reference value to determine whether or not a flaw is present in the welded portion.

5. A flaw detection method according to claim 1, wherein a plurality of ultrasonic wave detecting probes are aligned above the top face of the flange portion transversely of the welded portion and said probes are actuated in succession to scan the ultrasonic beams.

6. A flaw detection method according to claim 1, wherein said steel product is an H-beam shape steel.

7. An apparatus for the flaw detection of a T-welded portion of a steel product formed by T-welding a web member to a flange member, which comprises means for longitudinally moving the steel product while maintaining the flange portion horizontally, a frame member defining, together with the top face of the flange portion of the steel product being moved, a vessel containing an ultrasonic transmission medium therein, means for supplying the medium in said vessel, a convergent ultrasonic wave detecting probe disposed in said vessel to make ultrasonic waves incident on the top face of the flange substantially perpendicular to the top face of the flange through said medium, means for scanning ultrasonic beams of said detecting probe transversely of the line of intersection between the flange member and the web member, means for detecting echoes of the ultrasonic waves from a depth corresponding to the bottom face of the flange portion, and means for discriminating a flaw of the welded portion by synchronizing the detection of said echoes with the scanning position of said ultrasonic beams.

8. A flaw detection apparatus as set forth in claim 7, wherein the means for detecting echoes from a depth corresponding to the bottom face comprises a member for amplifying and detecting received waves of the probe, which is connected to said detecting probe, and means for comparing an output signal from said wave detecting member with a predetermined threshold value.

9. A flaw detection apparatus as set forth in claim 8, wherein the flaw discriminating means comprises a circuit generating a gate signal when the output of the wave detecting member is lower than the threshold value, an oscillator for generating pulse signals corresponding to the position of the detecting probe, a counter to be actuated on receipt of said gate signal to count said position pulse signals and a memory for storing the count value of said counter.

10. A flaw detection apparatus as set forth in claim 9, wherein the memory and the counter are constructed so that the memory receives a holding signal in correspondence to termination of one scanning of the detecting probe and the counter is reset after an elapse of a predetermined time from the time of termination of said one scanning.

11. A flaw detection apparatus as set forth in claim 7, wherein a plurality of detecting probes are arranged in the vessel of the medium to traverse the T-welded portion and the means for scanning the ultrasonic beams comprises a multiplexer for actuating said detecting probes in succession.

* * * * *